(12) United States Patent
Sauer et al.

(10) Patent No.: US 11,484,302 B2
(45) Date of Patent: Nov. 1, 2022

(54) MECHANICAL SUTURE FASTENER

(71) Applicant: LSI Solutions, Inc., Victor, NY (US)

(72) Inventors: Jude S. Sauer, Pittsford, NY (US);
Jason C. Patti, Rochester, NY (US)

(73) Assignee: LSI Solutions, Inc., Victor, NY (US)

( * ) Notice: Subject to any disclaimer, the term of this patent is extended or adjusted under 35 U.S.C. 154(b) by 365 days.

(21) Appl. No.: 16/741,873

(22) Filed: Jan. 14, 2020

(65) Prior Publication Data
US 2020/0222040 A1 Jul. 16, 2020

Related U.S. Application Data

(60) Provisional application No. 62/793,352, filed on Jan. 16, 2019.

(51) Int. Cl.
*A61B 17/04* (2006.01)

(52) U.S. Cl.
CPC .. *A61B 17/0401* (2013.01); *A61B 2017/0454* (2013.01)

(58) Field of Classification Search
CPC ........ A61B 17/0401; A61B 2017/0454; A61B 17/0487
See application file for complete search history.

(56) References Cited

U.S. PATENT DOCUMENTS

| 4,705,040 A | 11/1987 | Mueller |
| 5,160,339 A | 11/1992 | Chen |
| 5,300,078 A | 4/1994 | Buelna |
| 5,499,975 A | 3/1996 | Cope |
| 5,520,702 A | 5/1996 | Sauer |
| 5,643,289 A | 7/1997 | Sauer |
| 5,669,917 A | 9/1997 | Sauer |
| 5,735,875 A * | 4/1998 | Bonutti ............... A61F 2/30734 606/228 |
| 6,059,769 A | 5/2000 | Lunn et al. |
| 6,059,818 A * | 5/2000 | Johnson ............. A61B 17/0466 606/232 |

(Continued)

FOREIGN PATENT DOCUMENTS

| EP | 0669101 | 9/1999 |
| EP | 0669103 | 9/1999 |

(Continued)

OTHER PUBLICATIONS

May 30, 1995 Foreign Search Report; European Search Report for Patent No. EP 0 669 101.

(Continued)

*Primary Examiner* — Julian W Woo
(74) *Attorney, Agent, or Firm* — Michael E. Coyne; Christopher B. Miller

(57) ABSTRACT

A mechanical suture fastener includes a crimpable sleeve defining a channel therein. The crimpable sleeve also has a sleeve length, a channel diameter, and a sleeve length to channel diameter ratio of at least 4.0. The mechanical suture fastener also includes a flange joined to the crimpable sleeve on a distal end of the sleeve. The flange further includes a distal opening which is in communication with a proximal (Continued)

opening defined by the crimpable sleeve. The mechanical suture fastener also includes an inner flange radius of at least 0.007 inches.

11 Claims, 5 Drawing Sheets

(56) References Cited

U.S. PATENT DOCUMENTS

| | | | | |
|---|---|---|---|---|
| 6,464,713 | B2* | 10/2002 | Bonutti | A61F 2/30734 |
| | | | | 606/232 |
| 6,641,592 | B1 | 11/2003 | Sauer | |
| 7,235,086 | B2 | 6/2007 | Sauer | |
| 8,398,680 | B2 | 3/2013 | Sauer | |
| 9,017,382 | B2* | 4/2015 | Ogdahl | A61B 17/0401 |
| | | | | 606/232 |
| 10,076,377 | B2* | 9/2018 | Bonutti | A61B 17/12131 |
| 11,071,538 | B2* | 7/2021 | Boileau | A61B 17/56 |
| 2003/0204205 | A1 | 10/2003 | Sauer | |
| 2004/0015061 | A1 | 1/2004 | Currier et al. | |
| 2006/0020289 | A1 | 1/2006 | Kuttler | |
| 2007/0010829 | A1 | 1/2007 | Nobles | |
| 2009/0081313 | A1 | 3/2009 | Aghion | |
| 2014/0276979 | A1 | 9/2014 | Sauer et al. | |

FOREIGN PATENT DOCUMENTS

| | | |
|---|---|---|
| FR | 2682867 | 4/1993 |
| WO | WO1993009721 | 5/1993 |
| WO | WO1993014701 | 8/1993 |
| WO | WO2011126588 | 10/2011 |

OTHER PUBLICATIONS

May 30, 1995 Foreign Search Report; European Seach Report for Patent No. EP 0 669 103.

Sep. 20, 2011 International Search Report; International Search Report for PCT/US2011/021467.

Sep. 10, 2014 Foreign Search Report; Supplementary European Search Report for PCT US2011/021467.

Jun. 29, 2016 Office Action; Templeton, Christopher L.; For Related U.S. Appl. No. 14/325,824.

European Extended Search Report, dated Jun. 8, 2022, for EP Application No. 20741772.6, filed Jul. 6, 2021.

* cited by examiner

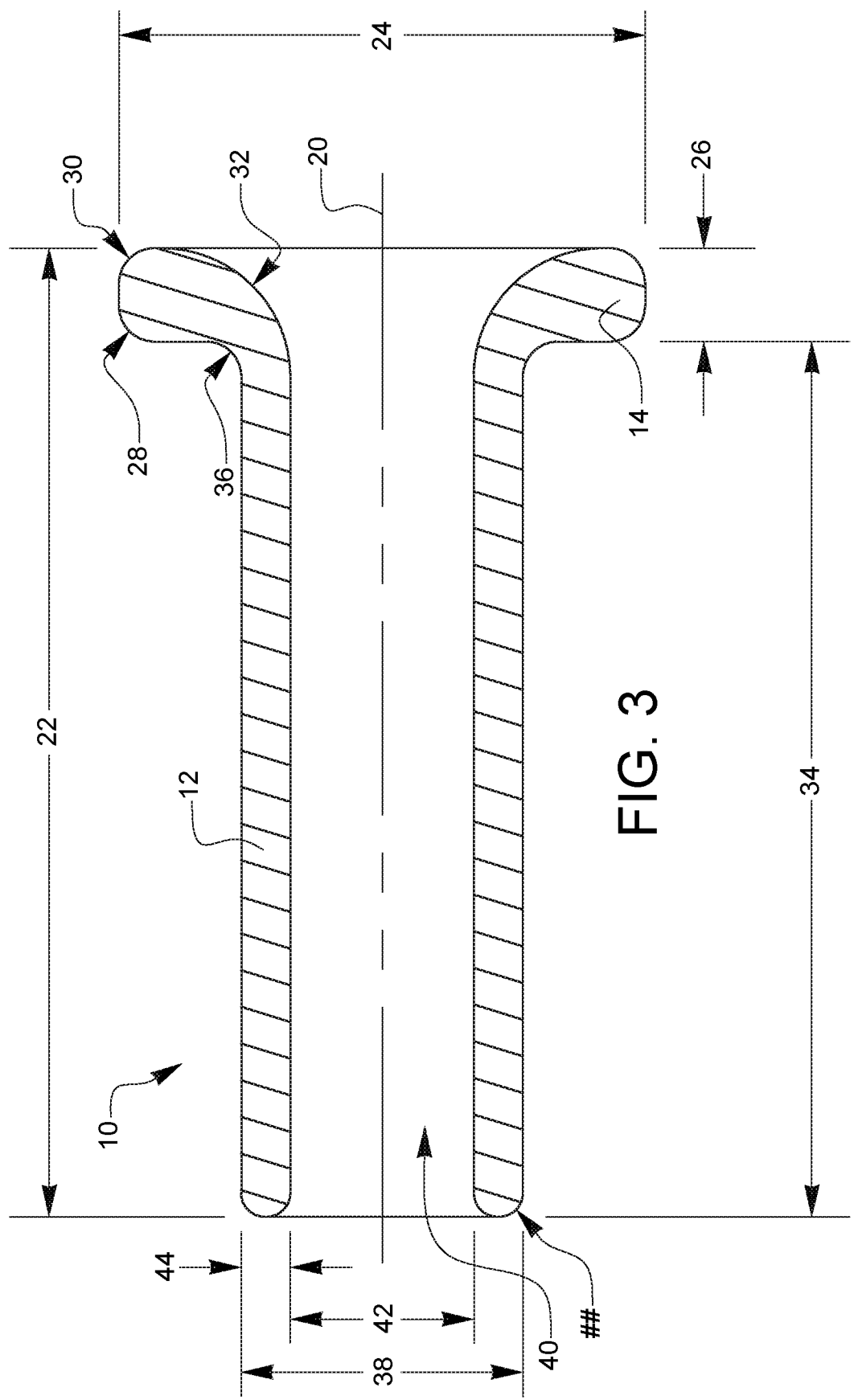

MECHANICAL SUTURE FASTENER

REFERENCE TO RELATED APPLICATIONS

This patent application claims priority to U.S. Provisional Patent Application No. 62/793,352 filed Jan. 16, 2019 and entitled "MECHANICAL SUTURE FASTENER." The 62/793,352 application is hereby incorporated by reference in its entirety.

FIELD

The claimed invention relates generally to surgical instruments for fastening suture, and more particularly to a mechanical fastener which is suitable for securing suture, particularly of very fine diameter.

BACKGROUND

Malleable suture fasteners such as the sleeves sold under the trademarks Ti-KNOT® and COR-KNOT® by LSI Solutions, Inc. are a significant improvement over hand or instrument-tied knots in laparoscopic surgical procedures. The sleeves, which are made of a malleable material that has proven safe with prolonged exposure to body tissue, are slid over two or more strands of suture and deformed or crimped to secure the strands of suture.

An exemplary crimping instrument is shown in U.S. Pat. No. 7,235,086, entitled "CRIMPING INSTRUMENT WITH MOTION LIMITING FEATURE", assigned to LSI Solutions, Inc., of Victor, N.Y. Such crimping devices have a handle with an actuator lever that is movable relative to the handle. A hollow shaft extends from the handle to a distal end of the shaft. Suture ends can be threaded through a crimping sleeve held between a hammer and an anvil which are located in the distal end of the shaft. The suture ends pass out a hole in the side of the shaft, and the device can be used to position the crimping sleeve at a desired location on the suture relative to a surface through which the suture has been secured (for example, tissue, a replacement anatomical structure such as a heart valve, or an augmentive anatomical structure such as a heart valve annulus).

Squeezing the actuator lever towards the handle causes a wedge, located in the shaft, to advance and to force the hammer into the crimping sleeve. The hammer crimps the crimping sleeve against the anvil, and the suture is held tightly by the deformed sleeve. A blade may also be incorporated within the shaft and can be simultaneously moveable by the actuator lever in order to trim the suture ends.

Such instruments for attaching suture fasteners have proven to be very effective for sutures of a 2-0 and a 3-0 size. The United States Pharmacopeia (U.S.P.) specifies suture sizes as follows:

| USP designation | Collagen diameter (mm) | Synthetic absorbable diameter (mm) | Non-absorbable diameter (mm) | American wire gauge |
|---|---|---|---|---|
| 11-0 | | | 0.01 | |
| 10-0 | 0.02 | 0.02 | 0.02 | |
| 9-0 | 0.03 | 0.03 | 0.03 | |
| 8-0 | 0.05 | 0.04 | 0.04 | |
| 7-0 | 0.07 | 0.05 | 0.05 | |
| 6-0 | 0.1 | 0.07 | 0.07 | 38-40 |
| 5-0 | 0.15 | 0.1 | 0.1 | 35-38 |
| 4-0 | 0.2 | 0.15 | 0.15 | 32-34 |
| 3-0 | 0.3 | 0.2 | 0.2 | 29-32 |
| 2-0 | 0.35 | 0.3 | 0.3 | 28 |
| 0 | 0.4 | 0.35 | 0.35 | 26-27 |
| 1 | 0.5 | 0.4 | 0.4 | 25-26 |
| 2 | 0.6 | 0.5 | 0.5 | 23-24 |
| 3 | 0.7 | 0.6 | 0.6 | 22 |
| 4 | 0.8 | 0.6 | 0.6 | 21-22 |
| 5 | | 0.7 | 0.7 | 20-21 |
| 6 | | | 0.8 | 19-20 |
| 7 | | | | 18 |

The 2-0 and 3-0 sutures (0.3 mm to 0.2 mm diameter) used with existing mechanical fastener products like the COR-KNOT® and Ti-KNOT® devices are useful in a wide range of surgeries where it is desired to approximate soft tissue and prosthetic materials. Unfortunately, these existing products are not indicated for use with smaller diameter sutures, such as, but not limited to 6-0, 7-0, and 8-0 sutures, which are much smaller in diameter (ranging from 0.07 mm down to 0.04 mm in diameter). These extremely small diameter sutures are useful in a wide variety of surgeries, such as coronary artery bypass graft (CABG) procedures, but it is not possible to use the existing COR-KNOT® or Ti-KNOT® crimpable sleeves (mechanical fasteners) with these small sutures. While these existing fasteners can be crimped onto such small suture, the sutures slip out of the fasteners under too low of a tension, making them incompatible.

It has been suggested that the dimensions of the COR-KNOT® fasteners simply be scaled down so that a proportionally smaller mechanical fastener could be used to secure smaller sutures, such as 6-0, 7-0, and 8-0 sutures. However, this has been attempted, including scaling down the critical portions of the device which crimps the mechanical fastener, and the results were not ideal. Hammer and anvil profiles, as well as mechanical fastener dimensions have proven not to be directly scalable to smaller suture, and as such design work related to different suture sizes from what is commercially available for mechanical suture fasteners is a non-obvious and highly exploratory endeavor.

Therefore, there is a need for a mechanical suture fastener which enables reliable suture holding performance when crimped onto 6-0, 7-0, and 8-0 suture.

SUMMARY

A mechanical suture fastener is disclosed. The mechanical suture fastener includes a crimpable sleeve defining a channel therein. The crimpable sleeve also has a sleeve length, a channel diameter, and a sleeve length to channel diameter ratio of at least 4.0.

The mechanical suture fastener also includes a flange joined to the crimpable sleeve on a distal end of the sleeve. The flange further includes a distal opening which is in communication with a proximal opening defined by the crimpable sleeve.

The mechanical suture fastener also includes an inner flange radius of at least 0.007 inches.

BRIEF DESCRIPTION OF THE DRAWINGS

FIG. 3 is a side cross-sectional view of the mechanical suture fastener of FIGS. 1A and 1B, illustrating relevant dimensions of the mechanical suture fastener.

Figure 1A:
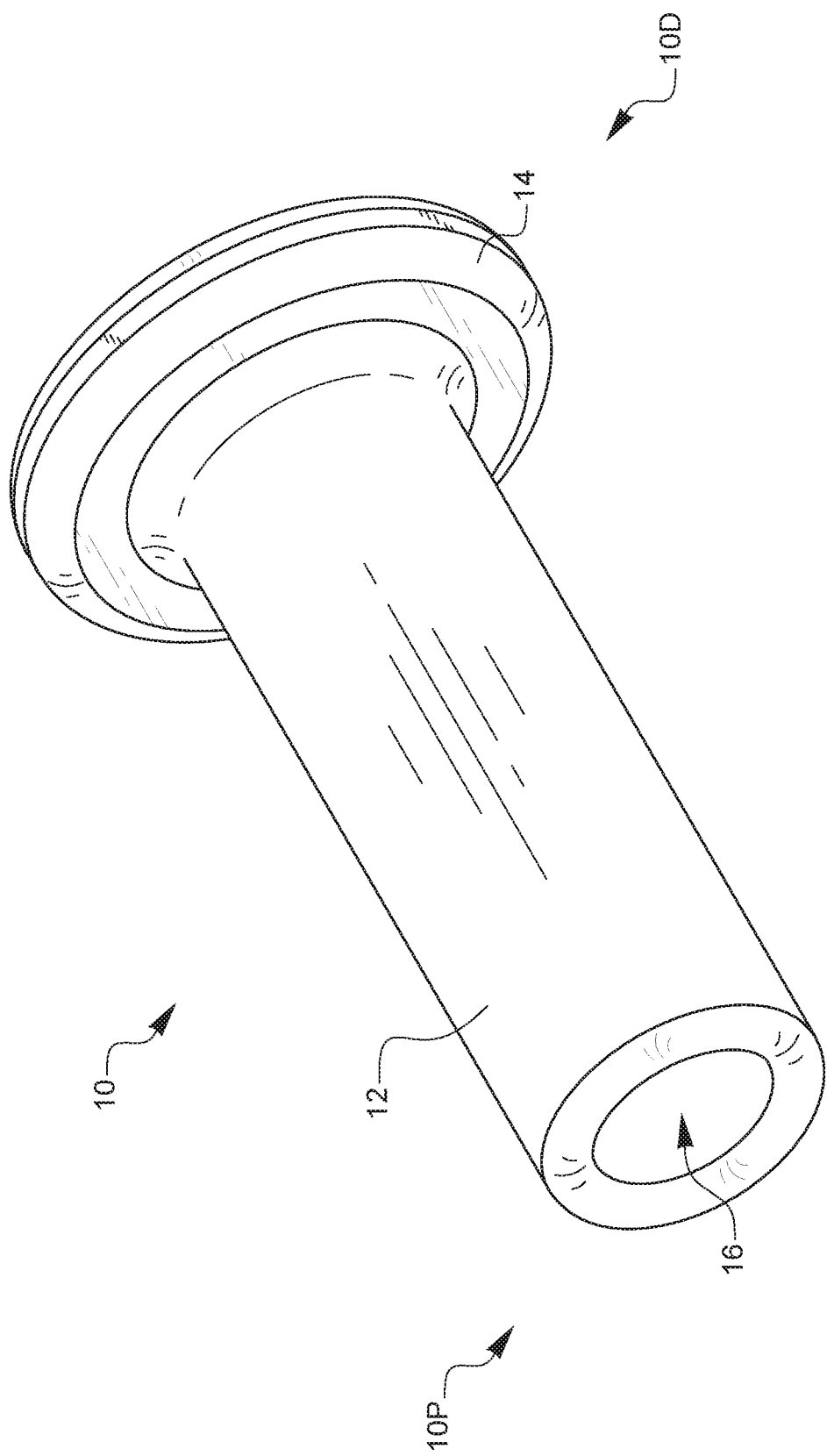
FIGS. 1A and 1B are proximal and distal perspective views, respectively, of one embodiment of a mechanical suture fastener.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 1B:
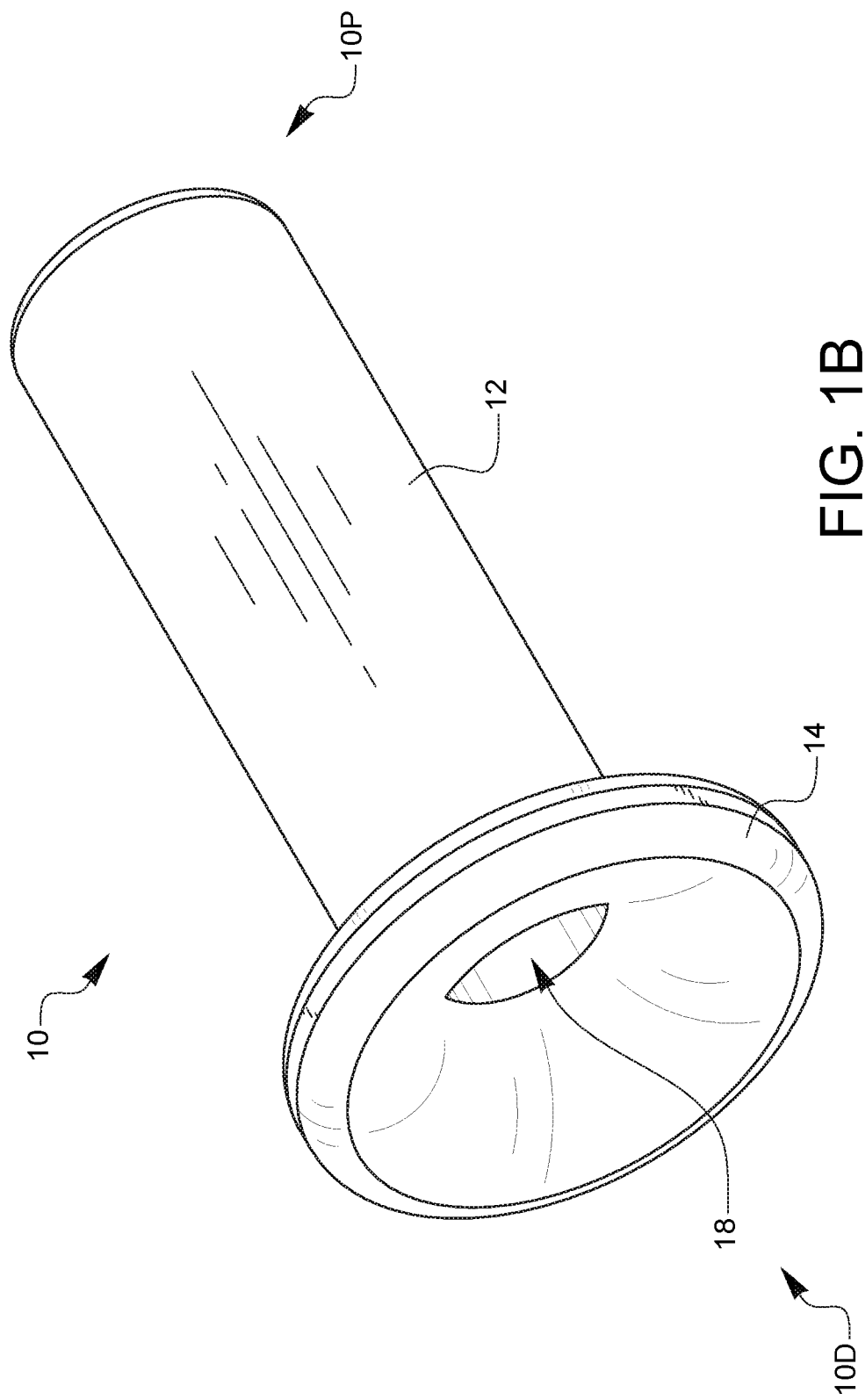

FIGS. 1A and 1B are proximal and distal perspective views, respectively, of one embodiment of a mechanical suture fastener. The mechanical suture fastener 10 ("fastener") has a crimpable sleeve 12 that joins a flange 14 on the distal end 10D of the sleeve 12. The crimpable sleeve 12 defines a proximal opening 16, and the flange 14 defines a distal opening 18. A channel is defined within the fastener, the channel allowing the proximal opening 16 to be in communication with the distal opening 18.

Figure 2A:
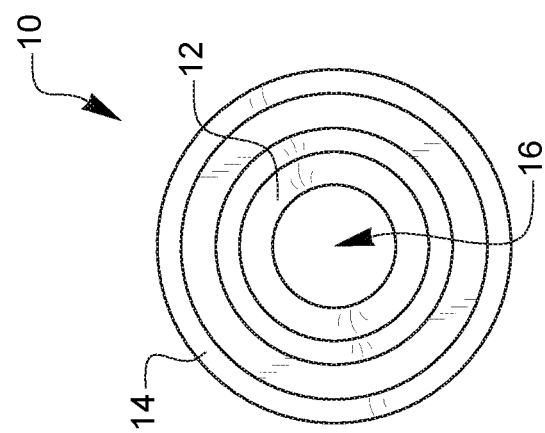
FIGS. 2A, 2B, and 2C are distal, side, and proximal elevational views, respectively, of the mechanical suture fastener of FIGS. 1A and 1B.
Figure 2B:
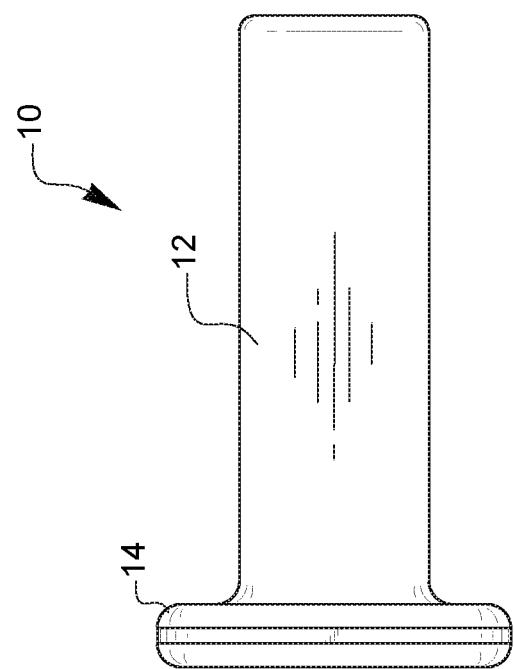
Figure 2C:
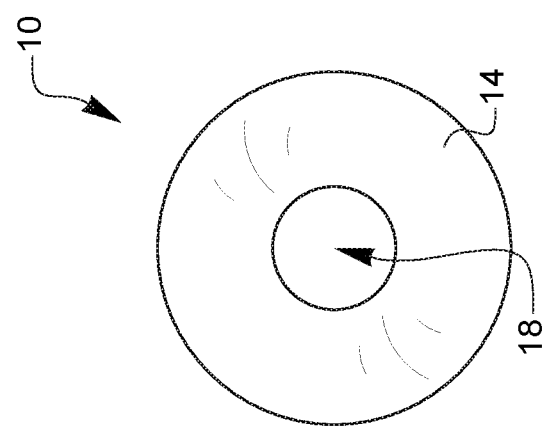

FIGS. 2A, 2B, and 2C are distal, side, and proximal elevational views of the fastener of FIGS. 1A and 1B.

FIG. 3 is a side cross-sectional view of a mechanical suture fastener, illustrating some relevant dimensions of the fastener. A longitudinal axis 20 of the fastener 10 is illustrated for an axial reference. A corresponding axial length 22 of the fastener is shown. The fastener also has a flange diameter 24 and a flange thickness 26. The flange 14 has a proximal outer flange radius 28, a distal outer flange radius 30, and an inner flange radius 32 as shown. The flange 14 further has a sleeve length 34 as shown, and a concave transition radius 36 between the flange 14 and the sleeve 12. The sleeve 12 has a sleeve diameter 38 measured on the outside of the sleeve 12, and the sleeve 12 defines a channel 40 having a channel diameter 42 on the inside of the sleeve 12. The crimpable sleeve 12 also has a wall thickness 44.

The table below illustrates different embodiments of different dimensions which have been discovered to provide suitable holding force and crimpable knot performance when used with 6-0, 7-0, and 8-0 suture.

It has been discovered that a crimpable mechanical fastener with an axial length to channel diameter ratio from about 5.19 to about 5.39 results in reliable suture holding force when the mechanical suture fastener is crimped onto 6-0, 7-0, or 8-0 suture. Similarly, it has been discovered that a crimpable mechanical fastener with a sleeve length to channel diameter ratio of about 4.69 to about 4.87 results in reliable suture holding force when the mechanical suture fastener is crimped onto 6-0, 7-0, or 8-0 suture. These ratios may be especially relevant for crimpable fasteners having a sleeve wall thickness of approximately 0.004 inches, but not necessarily limited to such thickness. The sleeve length to channel diameter ratio may be especially helpful in designing such fasteners, since it appears to be relatively independent of the flange dimensions, which may separately be chosen for criteria such as alignment of the mechanical suture fastener into a crimping device and for non-traumatic tissue interface. Other dimensional ratios and relationships are being explored in order to guide the designs for these types of fasteners, and such discoveries will be pursued in follow-on patent applications.

It has also been discovered that embodiments having an inner flange radius of approximately about 0.007 to 0.011 inches or larger, and preferably 0.011 inches or larger, may be helpful in preventing the mechanical suture fastener from cutting the 6-0, 7-0, or 8-0 suture held therein when the fastener has been crimped onto such suture. As mentioned with respect to other design parameters and dimensions of the mechanical suture fastener described herein, simply reducing the size of previously known embodiments of mechanical suture fasteners has proven ineffective in balancing desirable properties and quality measures such as reduced size, sufficient suture holding force while avoiding new issues such as suture cutting or shearing. Therefore, merely proportionally reducing dimensions or scaling down previous embodiments of mechanical suture fasteners resulted in an inner radius between the flange end and the inner channel that resulted in shearing or cutting the thinner 6-0, 7-0, or 8-0 suture which was held and crimped within the mechanical fastener.

Figure 4A:
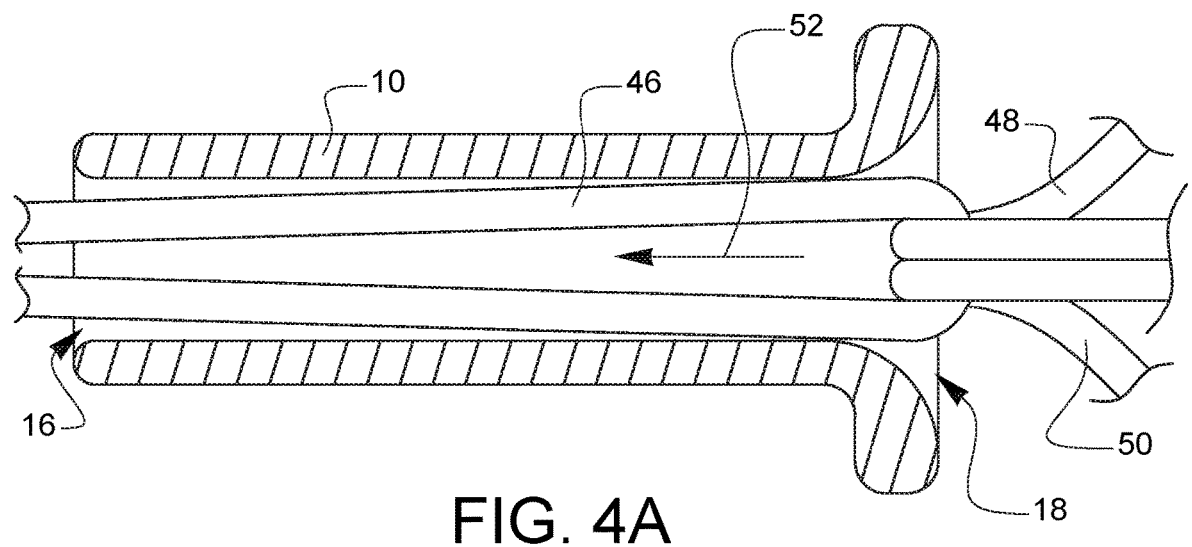
FIGS. 4A and 4B are side partial cross-sectional views of a mechanical suture fastener from two different elevations which are 90 degrees apart.
Figure 4B:
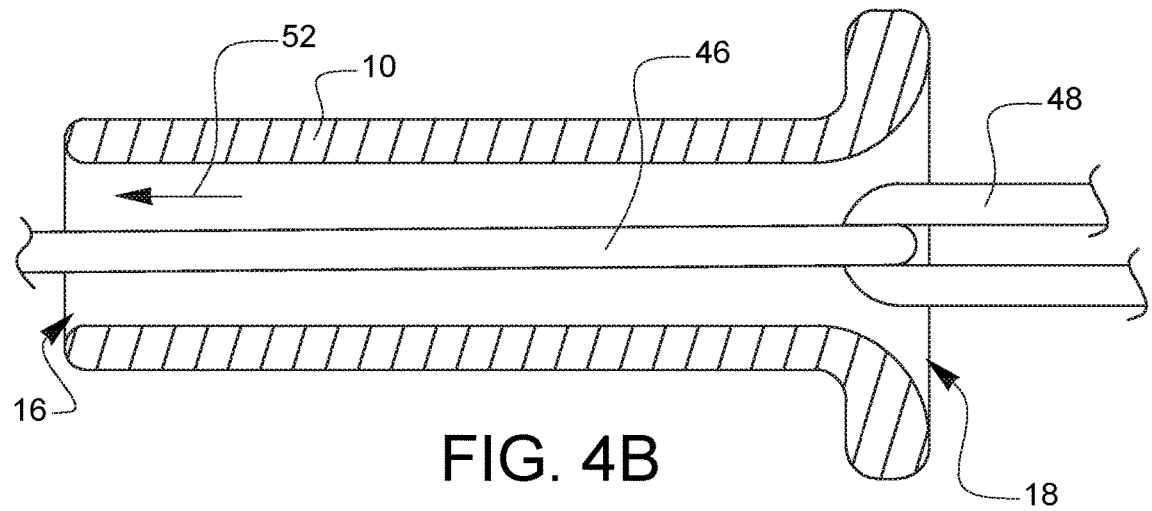

FIGS. 4A and 4B are side partial cross-sectional views of a mechanical suture fastener from two different elevations which are 90 degrees apart. They illustrate a snare wire 46 pulling first 48 and second 50 ends of a suture through the mechanical suture fastener in a proximal direction 52 (from the distal opening towards the proximal opening). Such a snare 46 may be used to load the suture ends 48, 50 (and therefore the suture) through the fastener 10 prior to a crimping action being performed on the fastener 10 in order to secure the suture therein. These views illustrate a design consideration for embodiments of crimpable fasteners which will employ a snare in such a scenario or similar scenarios.

| Measurement Description | Embodiment 1 Value (inches) | Embodiment 2 Value (inches) | Embodiment 3 Value (inches) | Embodiment 4 Value (inches) |
|---|---|---|---|---|
| Axial length | 0.083 | 0.083 | 0.083 | 0.083 |
| Channel diameter | 0.0160 | 0.0154 | 0.0160 | 0.0154 |
| Sleeve length | 0.075 | 0.075 | 0.075 | 0.075 |
| Concave transition radius | 0.003 | 0.003 | 0.003 | 0.003 |
| Proximal outer flange radius | 0.003 | 0.003 | 0.003 | 0.003 |
| Distal outer flange radius | 0.003 | 0.003 | 0.003 | 0.003 |
| Inner flange radius | 0.011 | 0.011 | 0.011 | 0.011 |
| Flange diameter | 0.040 | 0.040 | 0.045 | 0.045 |
| Flange thickness | 0.008 | 0.008 | 0.008 | 0.008 |
| Proximal sleeve radius | 0.0020 | 0.0020 | 0.0020 | 0.0020 |
| Sleeve diameter | 0.024 | 0.024 | 0.024 | 0.024 |
| Sleeve wall thickness | 0.004 | 0.004 | 0.004 | 0.004 |

It is important to size the channel diameter so it is at least large enough to allow the snare and the doubled-back suture ends to pass therethrough.

Various advantages of a mechanical suture fastener have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A mechanical suture fastener that is configured to retain one or more portions of suture having an approximate size of 6-0, 7-0, or 8-0, the mechanical suture fastener comprising:
    a sleeve extending along a longitudinal axis from a proximal end to a distal end, the sleeve having an interior surface and an exterior surface, with the interior surface defining at least a portion of a channel that extends from the proximal end to the distal end of the sleeve, wherein a sleeve length is a distance from the proximal end of the sleeve to the distal end of the sleeve along the longitudinal axis and the sleeve length is approximately 0.075 inches, wherein the interior surface has a cylindrical shape such that the channel has a circular cross-sectional shape having a channel diameter, wherein a sleeve length to channel diameter ratio is about 4.69 to about 4.87; and
    a flange that is coupled to the distal end of the sleeve such that a portion of the flange defines a distal opening of the channel, and wherein a proximal end of the interior surface of the sleeve defines a proximal opening of the channel that is in communication with the distal opening via the channel, and wherein the distal opening of the channel has a rounded portion comprising an inner flange radius of approximately about 0.007 inches to approximately about 0.011 inches,
    wherein the sleeve has a sleeve wall thickness and the flange has a flange thickness, and the flange thickness is greater than the sleeve wall thickness,
    wherein the channel is configured to receive the one or more portions of suture that is configured to extend through the channel from the proximal opening to the distal opening, and
    wherein the sleeve is configured to be deformed in a crimping operation performed on the exterior surface of the sleeve by a hammer and anvil disposed in a distal end of a shaft of a crimping device, the sleeve being deformed in a direction normal to the longitudinal axis such that the one or more portions of suture extending through the channel are secured within the channel by one or more portions of the interior surface of the deformed sleeve following the crimping operation.

2. The mechanical suture fastener of claim 1, wherein the sleeve wall thickness is approximately 0.004 inches.

3. The mechanical suture fastener of claim 2, wherein the flange thickness is approximately 0.008 inches.

4. The mechanical suture fastener of claim 3, wherein the proximal end of the interior surface of the sleeve and a proximal end of the exterior surface of the sleeve define a rounded proximal end, and wherein a proximal circumferential edge portion of the flange is rounded and a distal circumferential edge portion of the flange is rounded.

5. The mechanical suture fastener of claim 4, wherein a transitional edge disposed between a distal end of the exterior surface of the sleeve and a proximal portion of the flange is rounded.

6. The mechanical suture fastener of claim 1, wherein an axial length is a second distance from the proximal end of the sleeve to a distal end of the flange along the longitudinal axis.

7. The mechanical suture fastener of claim 6, wherein an axial length to channel diameter ratio is at least approximately 5.0.

8. The mechanical suture fastener of claim 6, wherein an axial length to channel diameter ratio is about 5.19 to about 5.39.

9. The mechanical suture fastener of claim 1, wherein the flange has a circular circumferential cross-sectional shape having a flange diameter of about 0.040 inches to about 0.045 inches.

10. The mechanical suture fastener of claim 1, wherein the circular cross-sectional shape of the channel is constant from the proximal end of the sleeve to the distal opening of the channel along the longitudinal axis.

11. The mechanical suture fastener of claim 10, wherein the exterior surface of the sleeve has a second circular cross-sectional shape that is constant from the proximal end of the sleeve to the distal end of the sleeve along the longitudinal axis.

* * * * *